(12) United States Patent
Huang et al.

(10) Patent No.: US 8,297,838 B2
(45) Date of Patent: Oct. 30, 2012

(54) EAR CAP SUPPLYING DEVICE, EAR CAP AND EAR CAP SET

(75) Inventors: Yi-Hsin Huang, New Taipei (TW); Chih-Chiang Yang, New Taipei (TW)

(73) Assignee: Taidoc Technology Corporation, New Taipei (TW)

( * ) Notice: Subject to any disclaimer, the term of this patent is extended or adjusted under 35 U.S.C. 154(b) by 45 days.

(21) Appl. No.: 13/152,396

(22) Filed: Jun. 3, 2011

(65) Prior Publication Data

US 2011/0299568 A1    Dec. 8, 2011

(30) Foreign Application Priority Data

Jun. 4, 2010    (TW) ............................... 99118336 A

(51) Int. Cl.
*G01K 1/08* (2006.01)
*G01K 1/00* (2006.01)

(52) U.S. Cl. ...................................... 374/209; 374/208

(58) Field of Classification Search ................. 374/208, 374/209
See application file for complete search history.

(56) References Cited

U.S. PATENT DOCUMENTS

| | | | |
|---|---|---|---|
| 2004/0016766 A1* | 1/2004 | Lin et al. | 221/191 |
| 2009/0122836 A1* | 5/2009 | Li | 374/209 |
| 2010/0116840 A1* | 5/2010 | Yu | 221/97 |
| 2010/0133291 A1* | 6/2010 | Yu | 221/97 |
| 2010/0147719 A1* | 6/2010 | Li | 206/438 |

* cited by examiner

*Primary Examiner* — Lisa Caputo
*Assistant Examiner* — Jamel Williams
(74) *Attorney, Agent, or Firm* — Chun-Ming Shih

(57) ABSTRACT

An ear cap supplying device, an ear cap and an ear cap set are provided. The ear cap supplying device includes a movable containing device and an output device. The movable containing device is used for containing at least one ear cap. The output device is used for exporting the ear cap(s). When the movable containing device is moved to a predetermined position, the movable containing device activizes the output device to export the ear cap(s). Whereby, problem that the ear cap(s) is/are obstructed during exporting process can be improved.

10 Claims, 18 Drawing Sheets

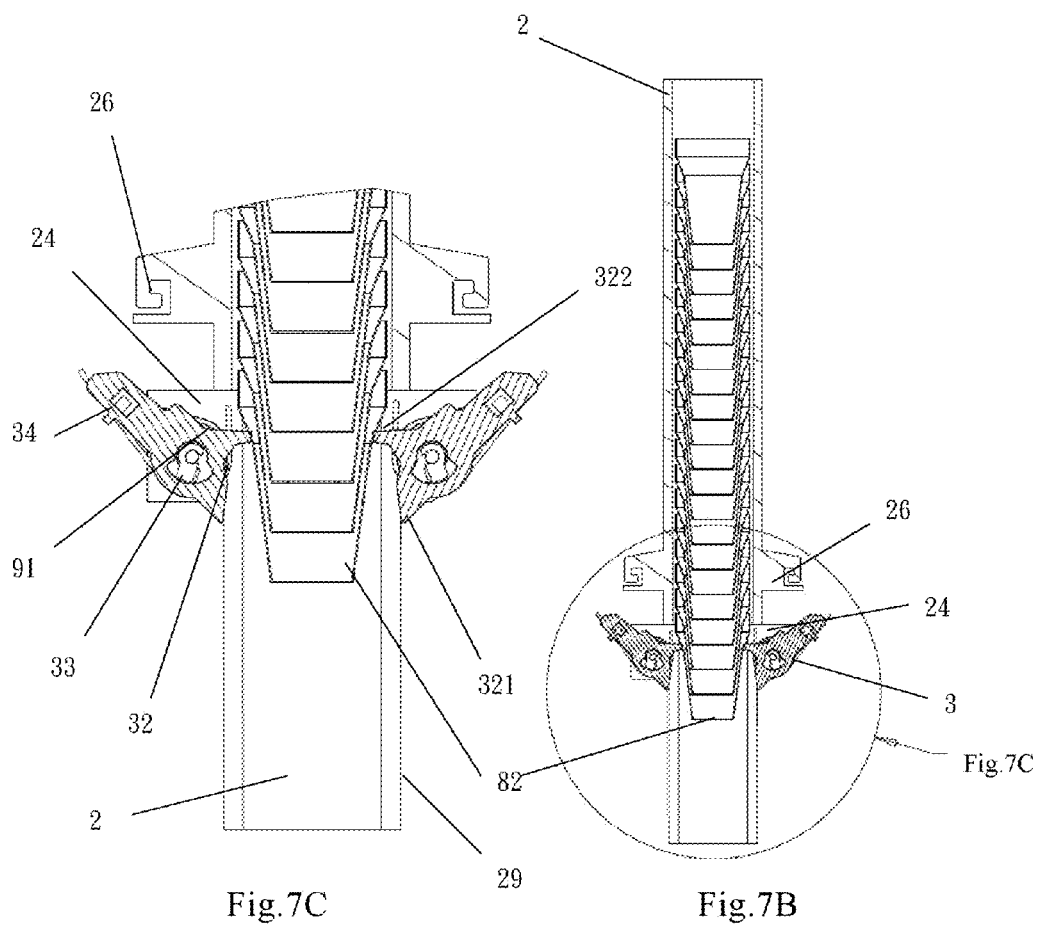

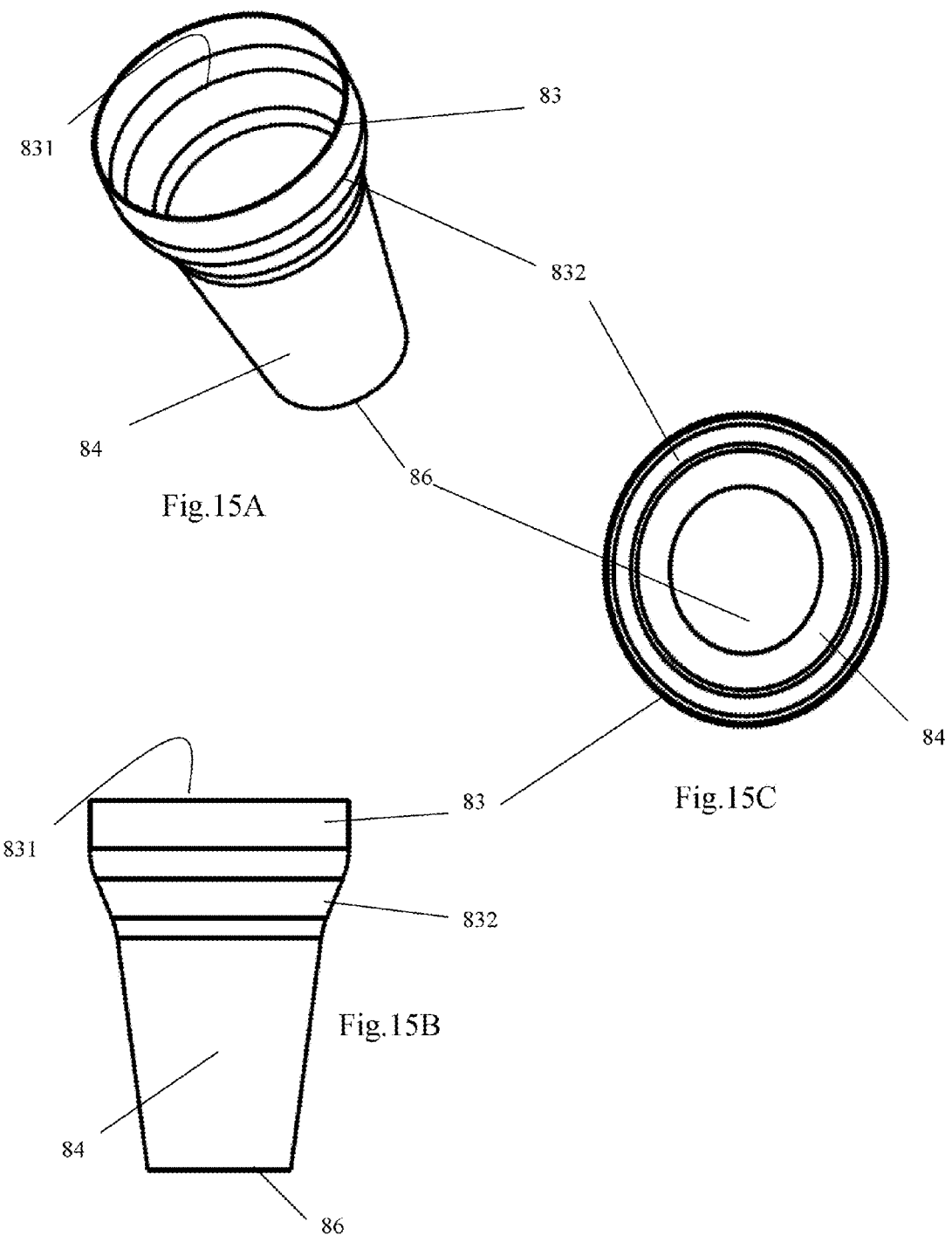

EAR CAP SUPPLYING DEVICE, EAR CAP AND EAR CAP SET

BACKGROUND OF THE INVENTION

1. Field of the Invention

The present invention relates to an ear cap supplying device, particularly relates to an ear cap supplying device with a movable containing device and an ear cap and an ear cap set adapted to it.

2. Description of the Related Art

With the advancement and prevalence of medical measuring technology, ear thermometer has already become an indispensable medical measuring device in hospital and homecare field. When using an ear thermometer, a sensor probe of the thermometer must be inserted into the external ear canal, and therefore, it is easy to have the probe polluted and then decrease the accuracy and durability of the ear thermometer.

Furthermore, there is also a risk of cross-infection while reusing the ear thermometer to different users. Hence, it is common to use a disposable ear cap to cover the sensor probe and change it after used to prevent from infection and maintaining the cleanness of the sensor probe.

However, while exchanging the ear cap by hands will not only increase the troublesome but also the possibility of being polluted.

To solve this problem, an ear cap cassette (301) referring to FIG. 1 is disclosed in the prior art. Multiple ear caps (100, 101) were placed in the ear cap cassette (301) in advance. Users may place an ear thermometer (107) into the ear cap cassette (301) to have a probe of the thermometer (107) covered by ear cap (101). However, this design will cause other unused ear caps to expose in the environment and increase the possibility of contacting with polluting sources.

Referring to FIG. 2, an ear cap dispenser is disclosed in the prior art. The ear cap dispenser comprises a base (102), an ear cap holding portion (103), an ear cap storing device (105) and an ear cap exporting slide (108). The ear cap holding portion (103) has a first opening (104). The ear cap storing device (105) has a second opening (106). In this design, ear caps can not be exported when blocked ear caps obstructed in the ear cap storing device (105). Furthermore, when an ear cap is exported from the ear cap storing device (105) to the ear cap holding portion (103) of the base (102), the ear cap must pass through the ear cap exporting slide (108). It will not only cause the ear caps to be blocked easily in the ear cap exporting slide (108) due to the friction force but also cause a problem that the ear caps can not enter the ear cap holding portion (103) accurately.

SUMMARY OF THE INVENTION

One aspect of the present invention is to provide an ear cap supplying device for adjusting the position of ear cap(s).

Another aspect of the present invention is to provide an ear cap supplying device including a movable containing device for containing ear cap(s).

Yet another aspect of the present invention is to provide an ear cap supplying device which can display the position situation of the ear cap(s).

Yet another aspect of the present invention is to provide an ear cap supplying device which can prevent ear cap(s) from directly contacting with the polluting sources.

Yet another aspect of the present invention is to provide an ear cap which is adapted to the ear cap supplying device described above.

Yet one another aspect of the present invention is to provide an ear cap set which is adapted to the ear cap supplying device described above.

In one aspect of the present invention, an ear cap supplying device is provided, which comprises a movable containing device and an output device. The movable containing device is used for containing at least one ear cap. The output device is used for exporting the ear cap(s). When the movable containing device is moved to a predetermined position, the movable containing device activizes the output device to export the ear cap(s).

In an embodiment of the present invention, the movable containing device may be any kind of shapes to form a space suiting with ear caps such as a tube-shaped, square-shaped, web shaped or pillar-shaped.

In an embodiment of the present invention, the output device can be an integrated structure member or multiple structure members engaged together.

The term "activize" described herein means directly or indirectly trigger, drive or promote and preferably herein is to drive the output device to export ear caps.

In an embodiment of the present invention, the output device may be engaged with the movable containing device. However, plenty of ways of the engagement can be designed, and therefore, it should not be limited by the embodiments described herein.

In an embodiment of the present invention, the output device comprises a first structural member and a second structural member. The first structural member movably supports a lower part of the above-mentioned ear cap. The second structural member movably touches an upper part of the above-mentioned ear cap.

In yet another embodiment of the present invention, the output device comprises a first structural member, a second structural member and a third structural member. The movable containing device is used for containing a first ear cap and a second ear cap. The second ear cap is stacked above the first ear cap. The first structural member movably supports a lower part of the first ear cap. The second structural member movably touches an upper part of the first ear cap. The third structural member movably supports a lower part of the second ear cap.

In an embodiment of the present invention, the first structural member or the third structural member described above comprises one or multiple supporting portion(s).

In an embodiment of the present invention, the second structural member described above comprises one or multiple touching portion(s).

In an embodiment of the present invention, the output device further comprises a forth structural member, a fifth structural member and a sixth structural member. The forth structural member movably supports the lower part of the first ear cap and is disposed at the opposite side from the first structural member. The fifth structural member movably touches the upper part of the first ear cap and is disposed at the opposite side from the second structural member. The sixth structural member movably supports the lower part of the second ear cap and is disposed at the opposite side from the third structural member.

In some embodiments of the present invention, the ear cap supplying device as described above further comprises a driving member. The driving member is coupled to the output device for driving the output device.

The driving member may be any structure to drive the output device such as a shield structure or a spring structure. The term "couple" means direct or indirect connection or engagement, herein is for driving the output device to change its position such as directly or indirectly being engaged with or touching the output device to drive.

In a preferred embodiment of the present invention, the ear cap supplying device further comprises a rail assembly. The rail assembly may be coupled to the movable containing device so that the movable containing device may be moved along the rail assembly. The rail assembly may be designed as a slide-style or a rotating-gear style or other styles.

In an embodiment of the present invention, the movable containing device comprises a main body and at least one extension portion. The main body is used for containing the ear cap(s). The extension portion extends out from the main body for providing a holding site.

The extension portion may be extended out from a side, top part or any outer part of the main body.

In an embodiment of the present invention, the ear cap supplying device further comprises an ear cap holding base. The ear cap holding base may be disposed at a site located at the path where the ear cap(s) exported out and is used for receiving the ear cap(s). As the movable containing device is moved from an initial position to the predetermined position, an opening of the ear cap supplying device will be relatively closer to the ear cap holding base.

The ear cap supplying device may be translucent, semi-translucent or opaque.

The movable containing device may be translucent, semi-translucent or opaque.

In an embodiment of the present invention, the ear cap supplying device further comprises an ear cap display device. The ear cap display device is used for displaying the disposing situation of the ear cap(s).

The ear cap display device may be designed such as an electrical sensing type, a transparent type or a digital type formed or disposed on the ear cap supplying device in accordance with the present invention. The disposing situation described herein can be such as the number of the ear caps or the position of the ear caps.

In another aspect of the present invention, an ear cap supplying device is provided, which comprises a movable containing device. The movable containing device is used for containing at least one ear cap and the position of the ear cap(s) may be adjusted with the motion of the movable containing device.

In an embodiment of the present invention, the motion may be such as sliding, shaking or vibrating motion.

In yet another aspect of the present invention, an ear cap adapted to an ear cap supplying device is provided. The ear cap supplying device described herein comprises a movable containing device. The ear cap described herein comprises a cover structure. The cover structure may fit in with a probe of an ear thermometer. The movable containing device is used for containing the ear cap. The position of the ear cap may be adjusted with the motion of the movable containing device.

In one another aspect of the present invention, an ear cap adapted to an ear cap supplying device is provided. The ear cap supplying device described herein comprises a movable containing device and an output device. The ear cap described herein comprises a cover structure which may fit in with the probe of an ear thermometer. The movable containing device is used for containing the ear cap(s), and when the movable containing device is moved to a predetermined position, the movable containing device activizes the output device to export the ear cap(s).

In yet one another aspect of the present invention, an ear cap set is provided. The ear cap set is adapted to an ear cap supplying device in accordance with the present invention. The ear cap supplying device comprises a movable containing device. The ear cap set comprises multiple ear caps and an ear cap holder. Each of the ear caps may fit in with a probe of an ear thermometer. The ear cap holder may holds the ear caps for next putting them into the movable containing device. The position of the ear cap(s) in the movable containing device may be adjusted with the motion of the movable containing device.

Accordingly, an ear cap supplying device is provided and with the motion of the movable containing device of the ear cap supplying device, the position of the ear caps in the movable containing device may be adjusted.

More exemplary embodiments and advantages of the present invention may be ascertained by reviewing the present disclosure and the accompanying drawing. It is intended that the description and embodiments with reference to the accompanying drawing to be considered as exemplary only.

BRIEF DESCRIPTION OF THE DRAWINGS

The invention will be further described, by way of example only, with reference to the accompanying drawings, in which:

FIG. 7B is a cross-sectional view of the tube-shaped movable containing device, the output device and the ear caps of the first embodiment referring to FIG. 7A;

FIG. 7C is a partially enlarged view referring to FIG. 7B;

FIG. 15A is a perspective view of the ear cap in accordance with the present invention;

FIG. 15B is a side view of the ear cap referring to the FIG. 15A; and

FIG. 15C is a top view of the ear cap referring to the FIG. 15A.

DESCRIPTION OF THE PREFERRED EMBODIMENTS

There are several problems in the prior art such as ear caps cannot be adjusted, exported smoothly or will possibly contact with the polluted sources.

In the contrast, an ear cap supplying device in accordance with the present invention comprises a movable containing device (or movable containing structure), a position of the ear caps may be adjusted by a motion of the movable containing device.

The following description and figures are some examples in accordance with the present invention. The same symbol herein in the figures indicates the same or similar structure.

With reference to FIGS. 3 to 9, those show a first embodiment of the present invention.

Figure 1:
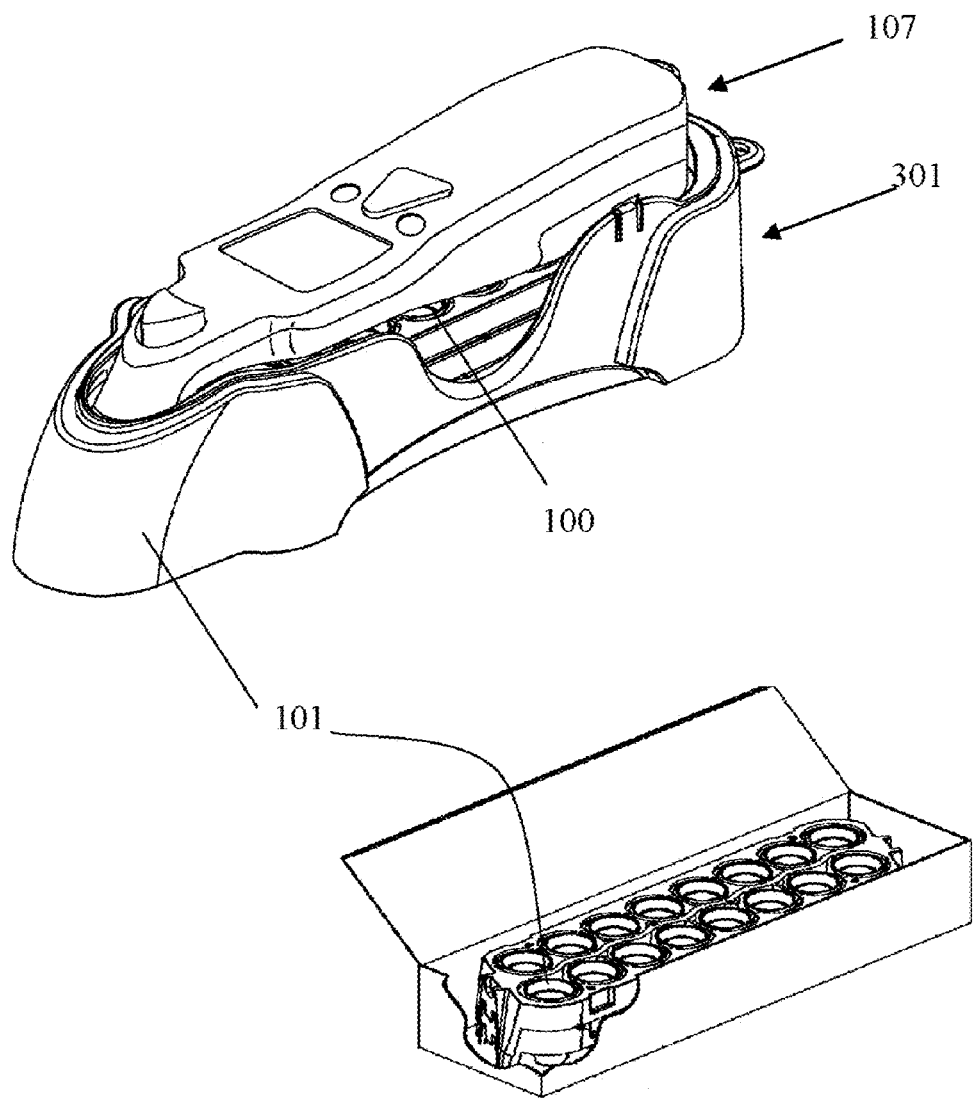
FIG. 1 is a view of a disclosed ear cap cassette in the prior art.
Figure 2:
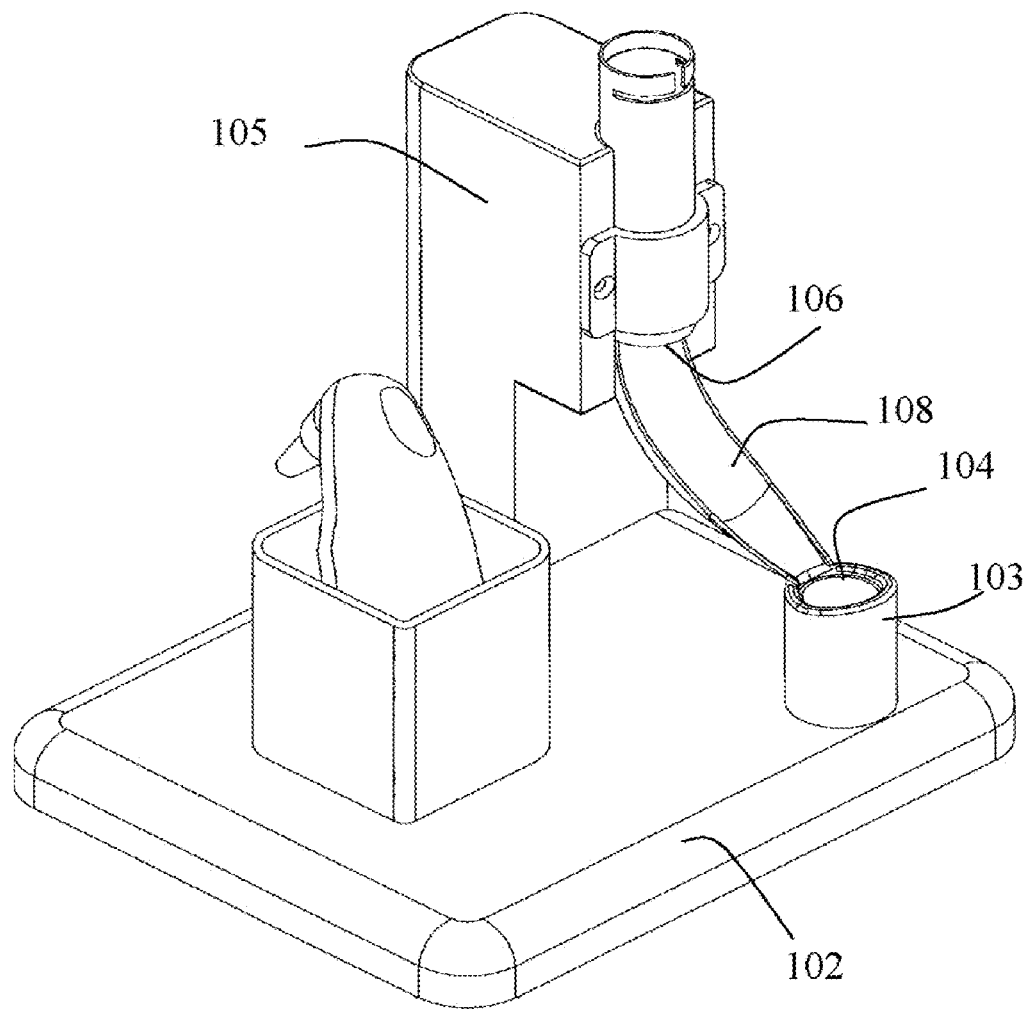
FIG. 2 is a view of a disclosed ear cap dispenser in the prior art.
Figure 3:
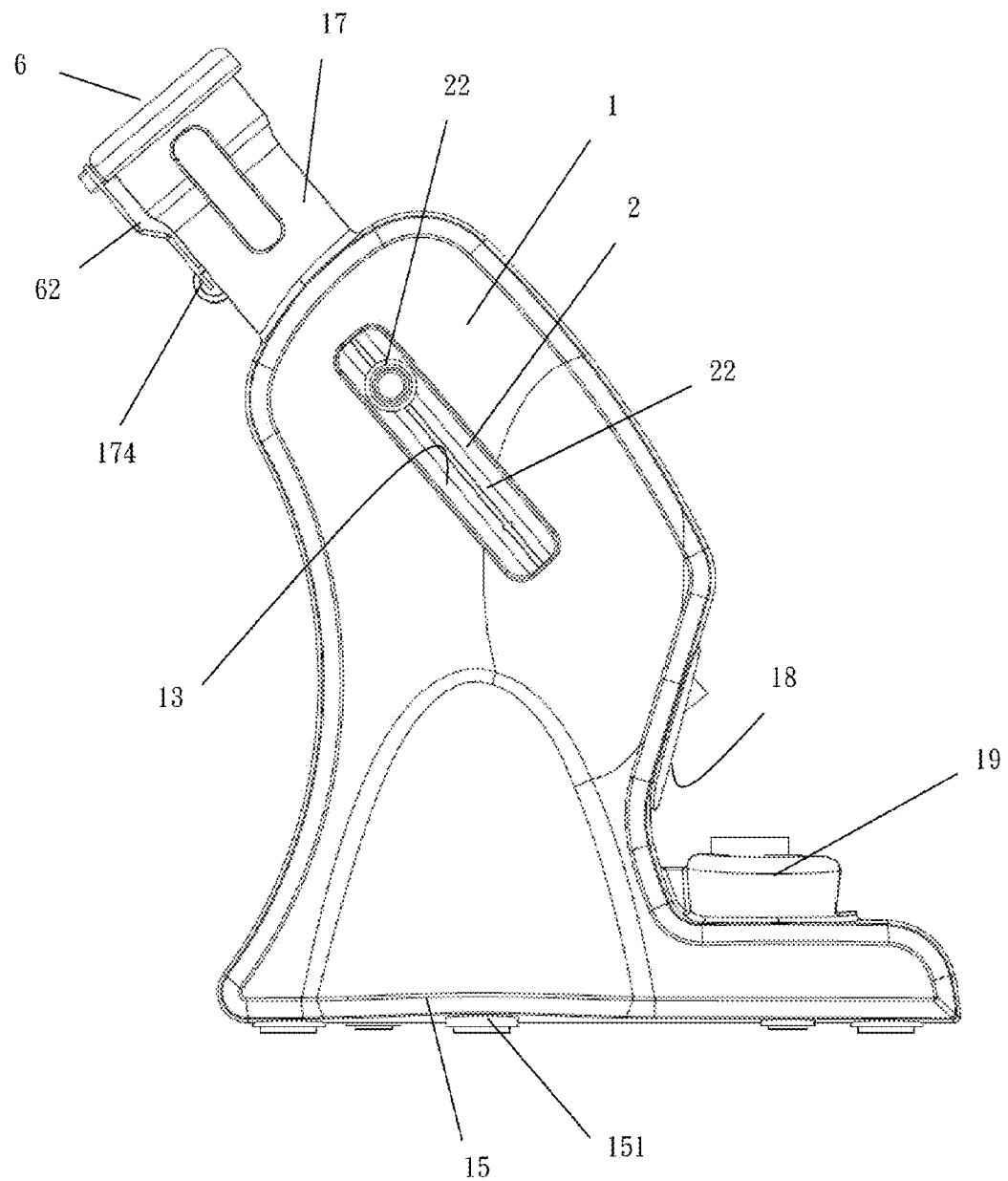
FIG. 3 is a side view of a first embodiment of an ear cap supplying device in accordance with the present invention.
Figure 4:
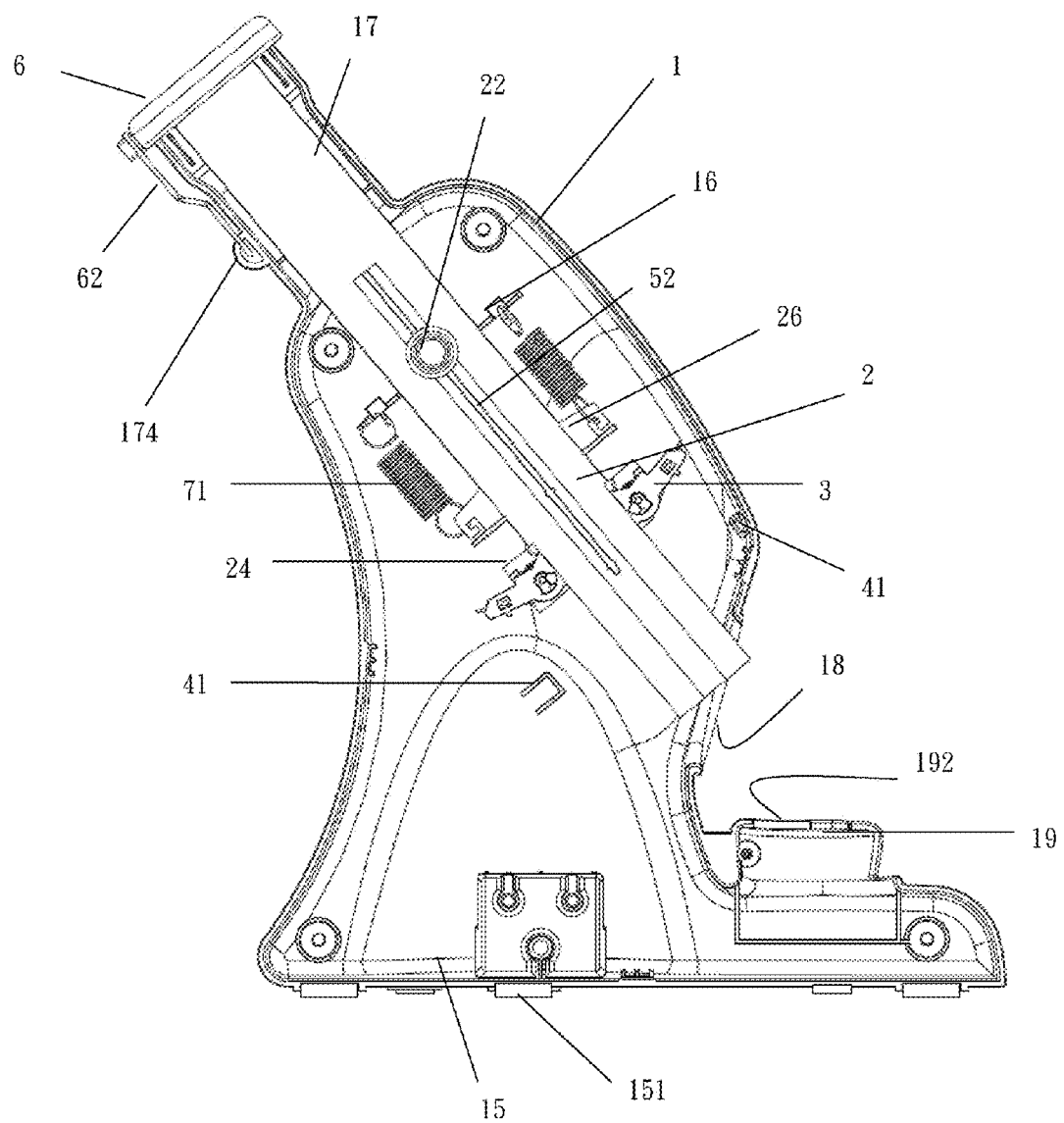
FIG. 4 is a partial cross-sectional view of the first embodiment in FIG. 3.
Figure 5:
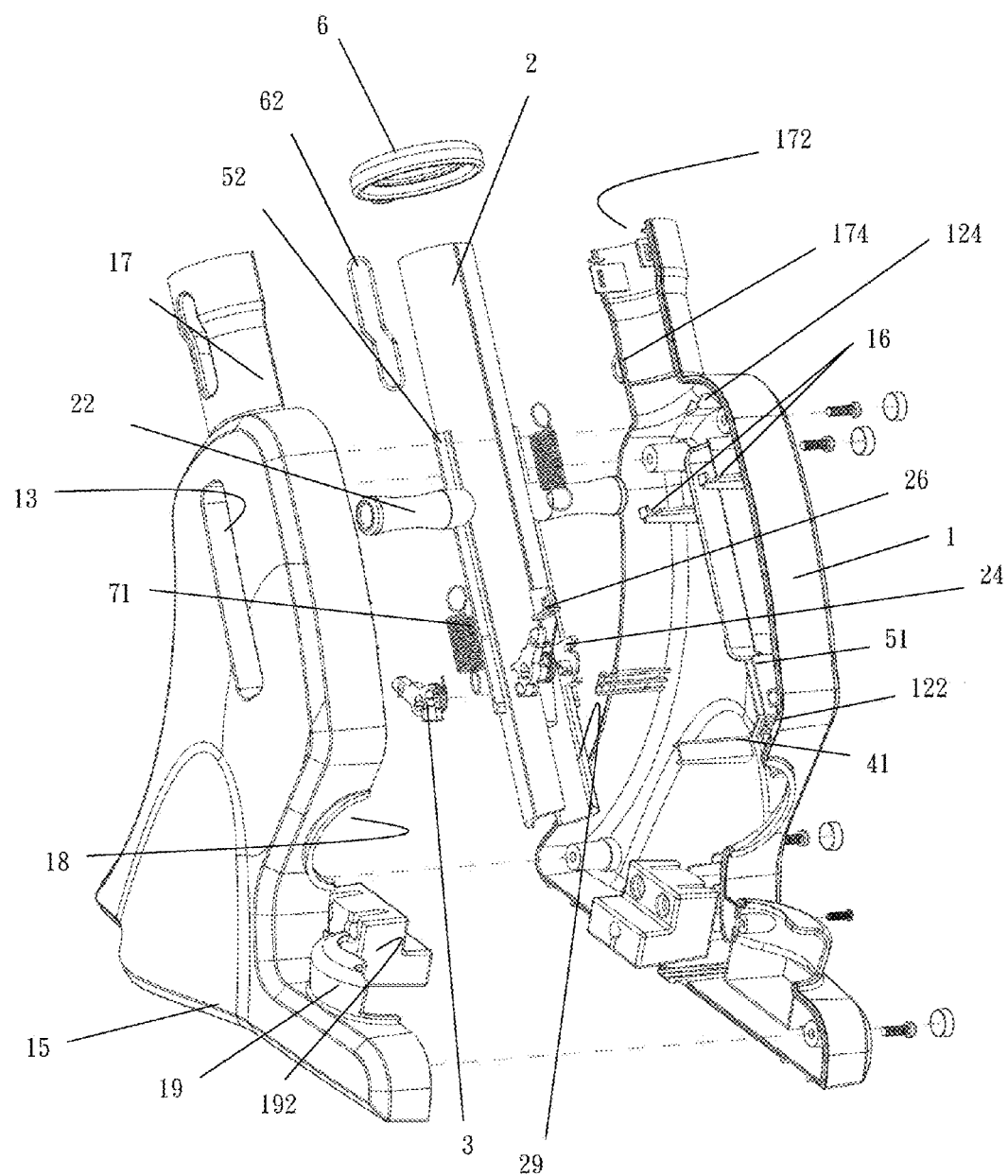
FIG. 5 is an exploded view of the first embodiment in FIG. 3.

Please refer to FIGS. 3 to 5 first. FIG. 3 is a side view of the first embodiment in accordance with the present invention. FIG. 4 is a partial cross-sectional view of the first embodiment in FIG. 3. FIG. 5 is an exploded view of the first embodiment in FIG. 3. The ear cap supplying device of the first embodiment in accordance with the present invention comprises a housing (1), a movable containing device (2) and an output device (3). The movable containing device (2) of the embodiment is tube-shaped. The output device (3) is as an arm structure. The movable containing device (2) is used for containing one or multiple ear cap(s) and is slidably engaged within the housing (1) and one end of the movable containing device (2) corresponds to a lower opening (18) of the housing (1). When the movable containing device (2) is moving, it can move through the lower opening (18).

Referring to FIG. 4 and FIG. 5, two half-housing parts are assembled to form the housing (1) in the first embodiment of the present invention. The housing (1) has the lower opening (18) and a driving member which is disposed near the lower opening (18) at an inner portion of the housing (1). In the embodiment of the present invention, the driving member is a shield (41) which may be couple or decoupled to the output device (3). The coupling way of the embodiment is when the movable containing device (2) moved to a predetermined position, the output device (3) will contact the shield (41).

Further referring to FIG. 5, two rail assemblies are disposed at two sides of the inner portion of the housing (1) respectively. Each of the rail assemblies has a slide (51) and a protrusion (52) correlated to the slide (51). The slide (51) is disposed at an upper site relative to the lower opening (18). The shields (41) may be disposed at two sides and next to the two slides (51) respectively, preferably near the lower opening (18). In the embodiment, two protrusions (52) protrude from two sides of the movable containing device (2) correlated to slides (51) respectively. Each of the protrusions (52) may be slidably coupled to the slide (51), and therefore, the movable containing device (2) can be engaged with the housing (1) and moving along a path of the slide (51) in the housing (1). Furthermore, a stopping portion (122) is further disposed at a lower end of the slide (51). The stopping portion (122) may restrict a moving path distance of the movable containing device (2) moving downwardly along the slide (51).

A detent portion (124) may be disposed at inner side of the housing upon the protrusion (52) for restricting a moving path distance of the movable containing device (2) moving upwardly along the slide (51). With the stopping portion (122) and detent portion (124), the moving path of the movable containing device (2) in the housing (1) can be restricted between the stopping portion (122) and detent portion (124) along the slide (51).

Figure 6A:
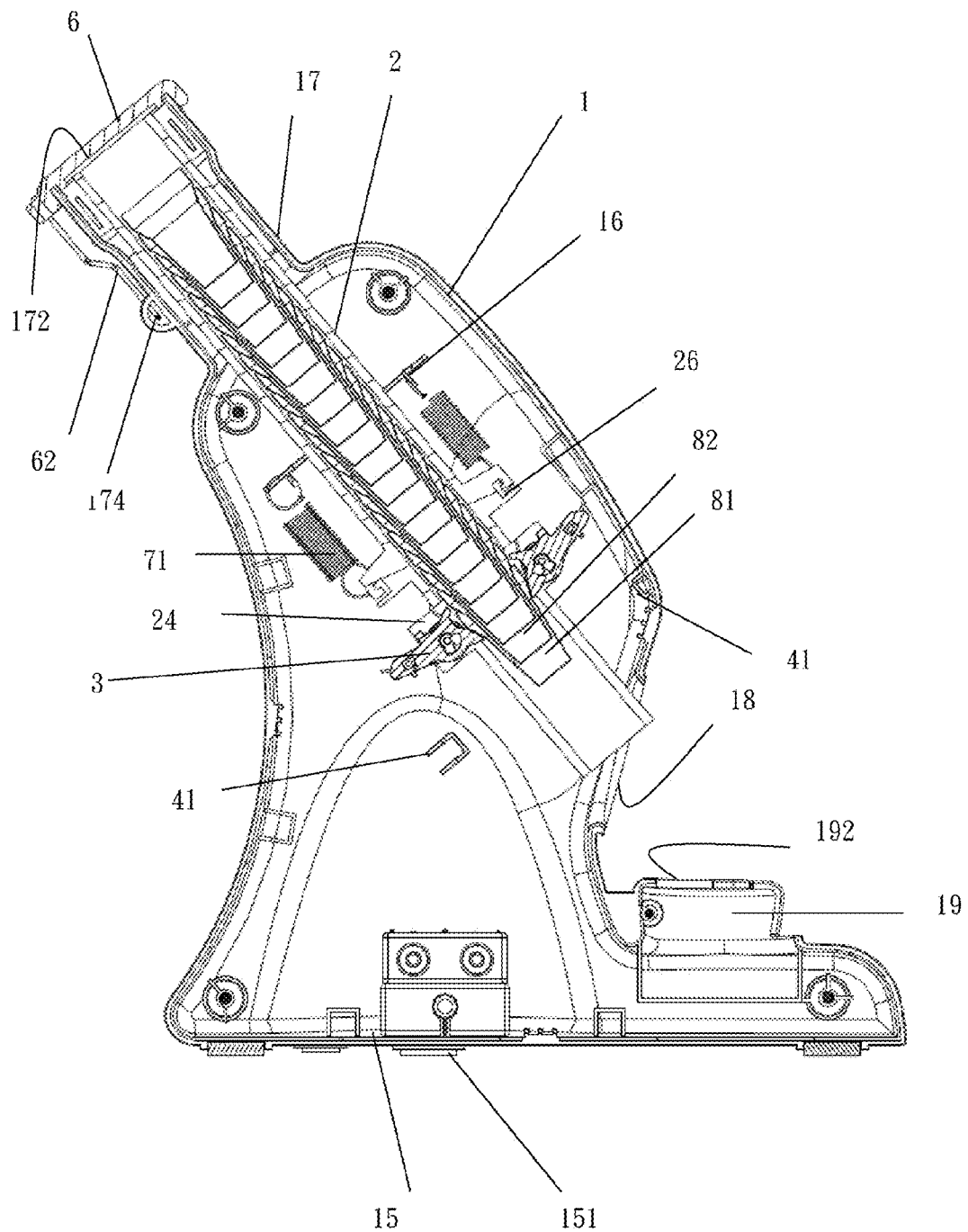
FIG. 6A is a partial side cross-sectional view of the first embodiment showing an output device untouched a shield.

Refer to FIG. 5 and FIG. 6A. FIG. 6A is a partial side cross-sectional view of the first embodiment showing the output device untouched the shield. The housing (1) of the ear cap supplying device further comprises a base (15). The base (15) has a base fixing member (151). The base (15) is used for locating the ear cap supplying device on a plane area. The base fixing member (151) is used for strengthening the connection between the base (15) and the plane area. Preferably, the base fixing member (151) can be made from materials with high friction coefficient, with viscidity or with magnetism. In another embodiment, the ear cap supplying device can be designed without the base (15), such as a hanging type which can be hanged on the wall.

In the first embodiment of the present invention, the housing (1) further includes an extended housing portion (17) extended upwardly from an upper end of the housing (1) with reference to FIG. 5. An upper end of the extended housing portion (17) has an upper opening (172). The extended housing portion (17) provides a space for the movable containing device (2) to move. Preferably, the upper opening (172) and the lower opening (18) of the housing (1) are set in the same axis. The movable containing device (2) is disposed between the upper opening (172) and the lower opening (18), and therefore, the ear caps can be put into the movable containing device (2) from the upper opening (172) and the output device (3) will be driven to have the ear cap exported out from the lower opening (18) by moving the movable containing device (2). In addition, in a middle position of the extended housing portion (17) is further defined a hanging hook (174). In other embodiments, the ear cap supplying device can be designed without a hanging hook (174).

The ear cap supplying device further comprises a cap (6). The cap (6) is connected with the hanging hook (174) by a line (62) and may be affixed onto the upper opening (172). One end of the line (62) is connected with the hanging hook (174) of the extended housing portion (17), and another end of the line (62) is connected with the cap (6). The ear cap(s) in the movable containing device (2) is prevented from being polluted when the cap (6) is affixed onto the upper opening (172). The hanging hook (174) and the line (62) can prevent losing the cap (6) when it is not affixed onto the upper opening (172).

In this embodiment of the present invention, the housing (1) further comprises an ear cap holding base (19). The ear cap holding base (19) is disposed corresponding to an extended downwardly position along the axial center of the movable containing device (2) and it may be extended upwardly from the base (15) of the housing (1) for receiving at least one ear cap exported from the lower opening (18) and for holding the ear cap in a stationary situation for future use. The ear cap holding base (19) has an opening (192) for receiving the falling ear cap successfully. When the ear cap is located in the ear cap holding base (19), a closure end of the ear cap won't contact a bottom of an inner part of the ear cap holding base (19) so as to prevent the ear cap from being polluting and deforming.

In this embodiment of the present invention, the housing (1) further has two channels (13) and each of them is disposed respectively at one of the two sides parallel to the axial center of the movable containing device (2). The movable containing device (2) further comprises an extension portion (22) and preferably there is two extension portions (22) respectively extended perpendicularly from the middle area of the two sides of the movable containing device (2). In this embodiment, the extension portion (22) is designed as a handle. The extension portion (22) passes through the channel (13) of the housing (1) for users to press in order to drive the movable containing device (2) to move slidably. Furthermore, the situation of the ear cap, such as the amount of the ear caps or the position of the ear caps, can be looked through the channel (13).

In other embodiments, an ear cap display device can be disposed on the ear cap supplying device and the ear cap display device can be an electrical sensing type, a transparent type or a digital type to achieve the display function as one of the function as the channel (13) is in the first embodiment of the present invention.

In another embodiment, the extension portion (22) may extend from a top of the movable containing device (2) through out the housing (1), so that users can have the movable containing device (2) moved by pressing the extension portion (22) on the top.

In the first embodiment of the present invention, the output device (3) is rotatably engaged with the movable containing device (2). A fixing member (24) is disposed at each of two sides of the movable containing device (2) and the output device (3) is rotatably coupled with the fixing member (24).

In other embodiments, the movable containing device (2) may be designed not to couple with the output device (3) and adjusting the position of the ear caps in the movable containing device (2) by moving the movable containing device (2).

Still referring to FIG. 5, the housing (1) further has two first joining hooks (16) respectively disposed at different sides of the slide (51). The movable containing device (2) further has two second joining hooks (26) respectively disposed at sides next to the protrusion (52). The second joining hook (26) is located at upper position relative to the fixing member (24) along a sidewall of the movable containing device (2). The first joining hook (16) extends inside from one side of the housing (1) and is disposed at upper position relative to the second joining hook (26) up along the slide (51).

The ear cap supplying device of the first embodiment further comprises a second driving member. The second driving member herein is a spring (71). One end of the spring (71) connects with the first joining hook (16) and another end of the spring (71) connects with the second joining hook (26). Due to the first joining hook (16) is disposed at the housing (1) and the second joining hook (26) is disposed at the movable containing device (2), the movable containing device (2) can be engaged with the housing (1) by the connection among the spring (71), first joining hook (16) and second joining hook (26).

Please, now refer to FIG. 6A. The movable containing device (2) is connected with the housing (1) by the spring (71). The output device (3) is connected with the movable containing device (2) by the fixing member (24). When the movable containing device (2) has not yet been moved, the output device (3) can support at least one ear cap such as ear caps (81, 82) as drawing showed in the movable containing device (2) and hold the ear cap (81, 82) without falling out. During this time, the output device (3) keeps a distance from the shield (41) to not contact with the shield (41).

Figures 6B, 6C:
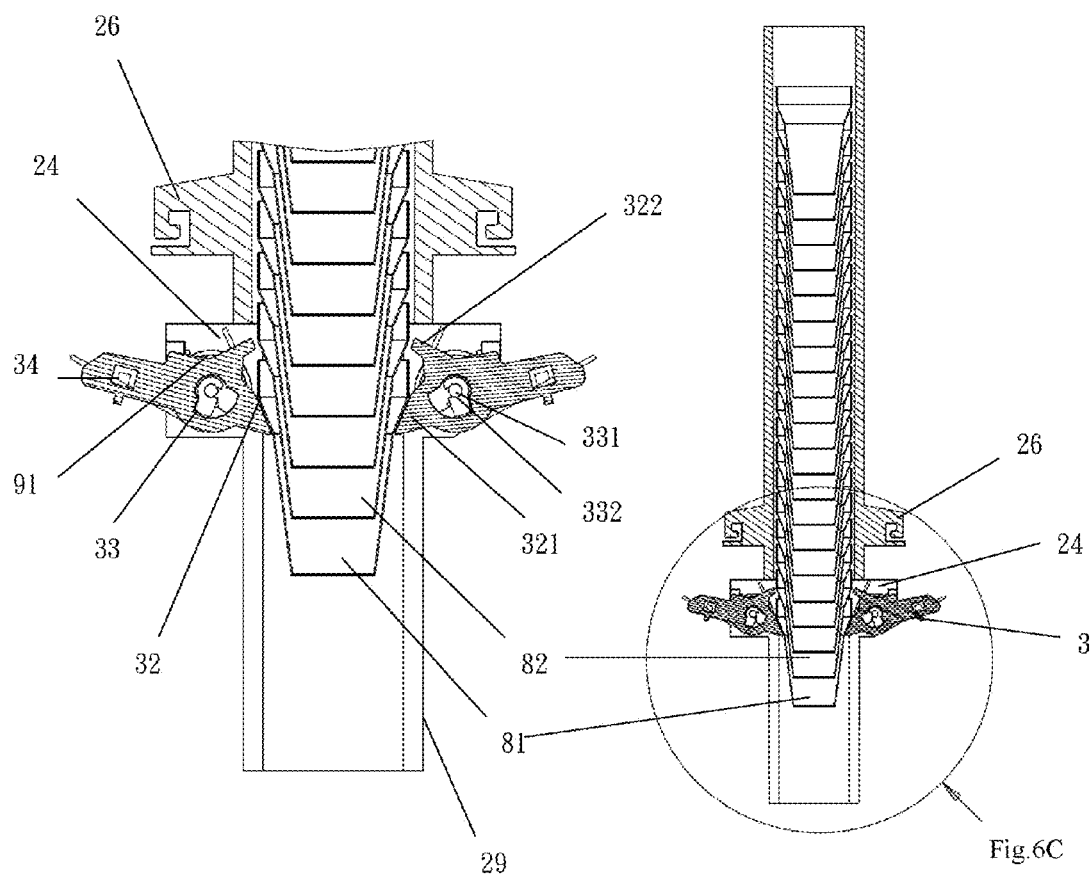
FIG. 6B is a cross-sectional view of a tube-shaped movable containing device, the output device and ear caps of the first embodiment referring to FIG. 6A.
FIG. 6C is a partially enlarged view referring to FIG. 6B.

With reference to FIG. 6B and FIG. 6C, FIG. 6B is a cross-sectional view of the tube-shaped movable containing device, the output device and the ear caps of the first embodiment referring to FIG. 6A. FIG. 6C is a partially enlarged view referring to FIG. 6B.

The output device (3) comprises an ear cap supporting portion (32) and a rotation portion (33). In the first embodiment of the present invention, the supporting portion (32) includes ribs (321, 322). Ribs (321, 322) support the ear caps in the movable containing device (2). The rotation portion (33) includes a rotating hole (331) and a rotating shaft (332) passed through the rotating hole (331), which makes the output device (3) rotatable. In other embodiment, the ear cap supporting portion (32) may include more than two ribs.

Furthermore, a divided portion (29) is defined at a lower end of the movable containing device (2), which can be located at the same side as the fixing member (24) is, and extends upwardly from the lower end of the movable containing device (2) to at least the position relative to the fixing member (24). The ribs (321, 322) of the output device (3) contact with the ear caps in the movable containing device (2) by passing through the divided portion (29).

When the output device (3) does not contact the shield (41) as FIG. 6A shown, the rib (321) supports the ear cap (81) as FIGS. 6B and 6C shown, and more specifically, the rib (321) supports a lower part of the ear cap (81) in the movable containing device (2) for preventing the ear caps from falling.

Figure 7A:
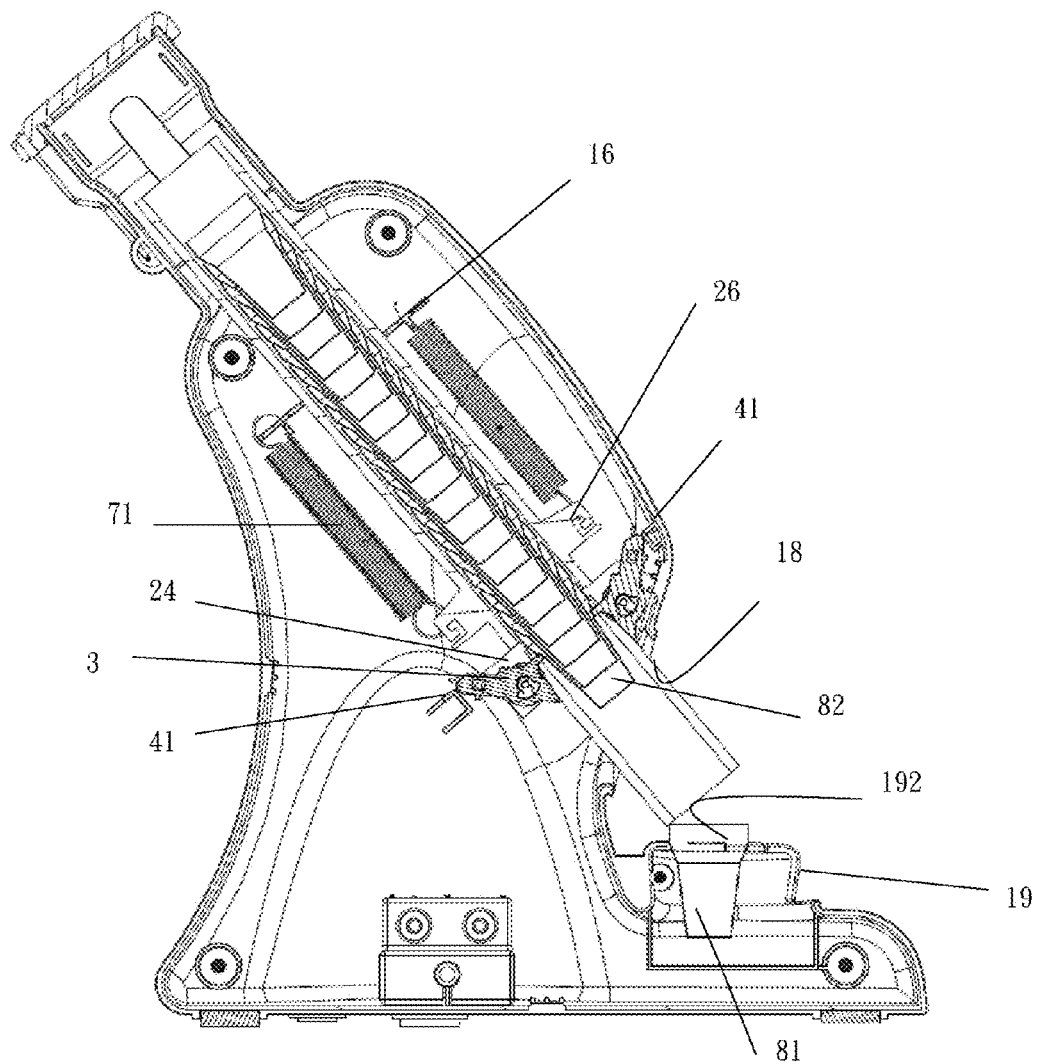
FIG. 7A is a partial side cross-sectional view of the first embodiment in accordance with the present invention after the output device touches the shield.

Now referring to FIGS. 7A to 7C, FIG. 7A is a partial side cross-sectional view of the first embodiment during the output device contacts the shield. FIG. 7B is a cross-sectional view of the tube-shaped movable containing device, the output device and the ear caps of the first embodiment in FIG. 7A. FIG. 7C is a partially enlarged view referring to FIG. 7B.

When user moves the movable containing device (2) downwardly, the output device (3) will be driven to move (or rotate) by contacting with the shield (41) with reference to FIG. 7A. Furthermore, the spring (71) is extension to storage energy by the motion of the movable containing device (2) for next moving the movable containing device (2) back to its initial position.

Referring to FIGS. 7B and 7C, the output device (3) further includes a shield touching portion (34). A third driving member is further engaged between the fixing member (24) and the output device (3). The driving member herein is a spring (91).

Please also referring to FIG. 7A, the movable containing device (2) is moved to the position that the shield touching portion (34) of the output device (3) touches the shield (41). Keeping moving the movable containing device (2) downwardly, the output device (3) will keep being driven to rotate (or move) and then the position of the ear caps in the movable containing device (2) in relation to the ear cap supporting portion (32) of the output device (3) will be changed.

Firstly, the rib (322) of the output device (3) will support the ear cap (82) upon the ear cap (81), more specifically support a lower part of the ear cap (82), to prevent other ear caps to fall down except the ear cap (81). Meanwhile, the movable containing device (2) keeps moving downwardly, the rotation portion (33) may keep being driven to rotate, and the rib (321) of the output device (3) will leave away from the ear cap (81) to have the ear cap (81) fallen down out from the lower opening (18) and into the ear cap holding base (19) through the opening (192). Moreover, keep rotating the rotation portion may lead the rib (322) to touch the ear cap (81), more specifically touch an upper part of the ear cap (81), and then push the ear cap (81) to the lower opening (18) to insure the ear cap (81) falling down smoothly. Therefore, the rib (322) is not only used for supporting the ear cap (82) but also pushing the ear cap (81) to fall down. The spring (91) here is used for storage energy to let the output device (3) move (or rotate) back to its initial situation before touching the shield (41).

Please then referring back to both FIGS. 7A and 7C, when the shield touching portion (34) touches the shield (41), the position of the movable containing device (2) is closer to the opening (192) so that an opening at the lower end of the movable containing device (2) is located right upon the opening (192). Due to the motion of the movable containing device (2) to a position that the shield touching portion (34) of the output device (3) touches the shield (41), it will let the ear cap (81) to fall down by keeping moving the movable containing device (2). Therefore, by moving the movable containing device (2) closer to the opening (192) may make ear cap (81) to fall down accurately to the ear cap holding base (19) from the opening at lower end of the movable containing device (2).

Figure 8A:
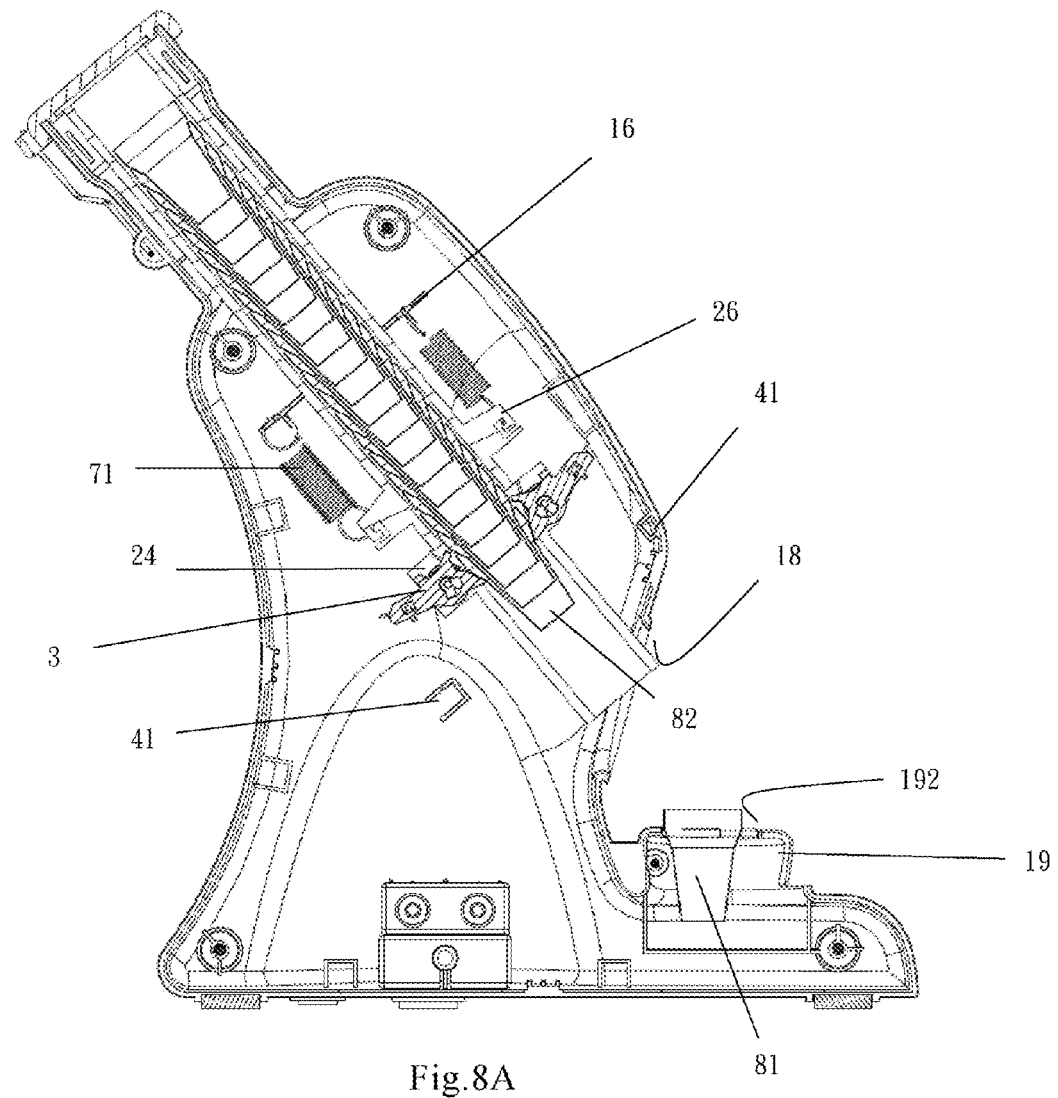
FIG. 8A is a partial side cross-sectional view of the first embodiment showing the output device removed to its original position.

Now referring to FIG. 8A, it is a side cross-sectional view of the first embodiment showing the output device removes back to its initial position. At this time, the ear cap (81) fell down into the ear cap holding base (19) by moving the movable containing device (2). If the force from the outside (from users) ceases, the resilience energy of the spring (71) will be released to drive the movable containing device (2) upwardly move back to its initial position without contacting with the shield (41) as FIG. 8A shown.

Figures 8B, 8C:
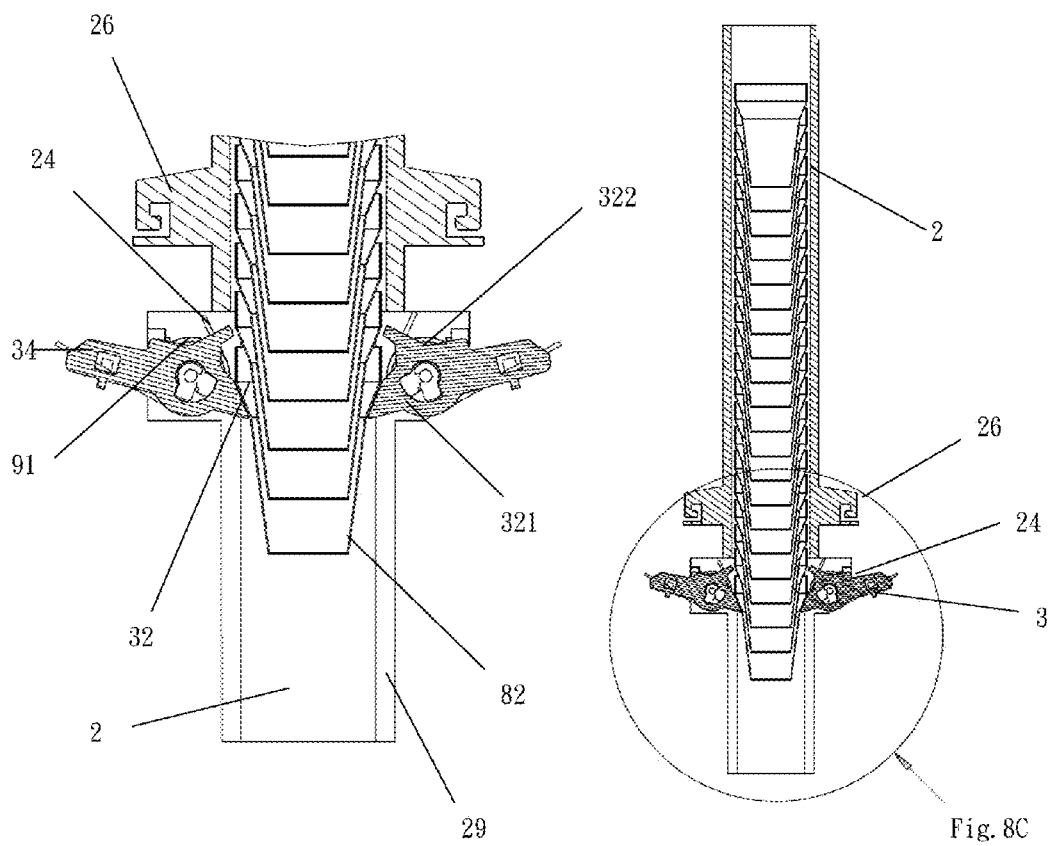
FIG. 8B is a cross-sectional view of the tube-shaped movable containing device, the output device and the ear caps of the first embodiment referring to FIG. 8A.
FIG. 8C is a partially enlarged view referring to FIG. 8B.

Referring to FIGS. 8B and 8C, FIG. 8B is a cross-sectional view of the tube-shaped movable containing device, the output device and the ear caps of the first embodiment in FIG. 8A. FIG. 8C is a partially enlarged view referring to FIG. 8B.

When the movable containing device (2) and the output device (3) remove back to its initial position due to the force from outside (from the user) released with reference to FIG. 8A, rib (321) supports the ear cap (82), more specifically supports a lower part of the ear cap (82), to let the ear caps held in the movable containing device (2) and prevent from falling out as FIGS. 8B and 8C shown. By the operation from moving the movable containing device (2) to a predetermined position and then removing it back to its initial position, one run of an ear cap supplying will be completed.

Figure 9:
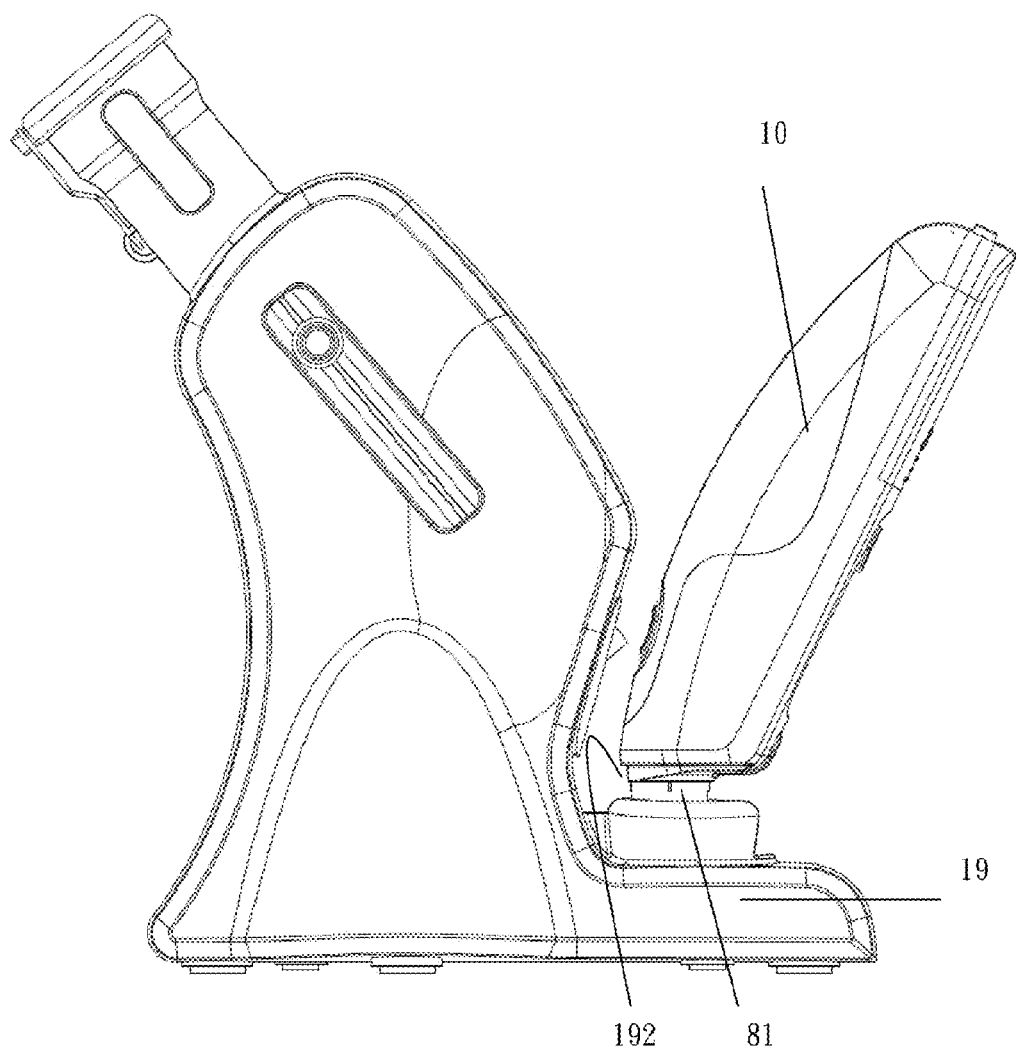
FIG. 9 is a side view of the first embodiment in accordance with the present invention showing the ear cap supplying device adapted to a thermometer.

Referring to FIG. 9, FIG. 9 is a side view of the first embodiment in accordance with the present invention showing the ear cap supplying device is adapted to a thermometer. After using the ear cap supplying device according to the operation described above, ear cap (81) falls down into the ear cap holding base (19) and a cap opening of the ear cap (81) is exposed outside the opening (192), hence, the probe of the thermometer may be inserted into ear cap (81) and have the ear cap covered the probe of the ear thermometer. Therefore, the polluted problem can be solved by not touching the ear caps by users. In this embodiment, the thermometer is an IR ear thermometer but should not be limited.

Although possible types of ear cap supplying devices, ear caps and ear cap sets in accordance with the present invention have been described in the embodiments above, those skilled in the art shall recognized that different ear cap supplying devices, ear caps and ear cap sets can be designed. Therefore, the spirit of the present invention shall not be limit to these possible types of the ear cap supplying devices, the ear caps, or the ear cap sets in accordance with the present invention. In other words, an ear cap supplying device with a movable containing device for adjusting the position of the ear cap(s) or which further including an output device for letting the ear cap(s) to be exported is the key spirit and scope of the present invention. The followings are some other embodiments in accordance with the present invention for those skilled in the art to know more specifically about the spirit of the present invention.

Figure 10A:
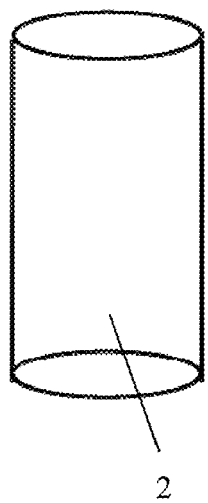
FIGS. 10A to 10C are abridged general views of some types of the movable containing device in accordance with the present invention.
Figure 10B:
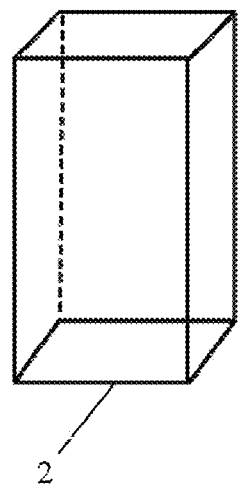
Figure 10C:
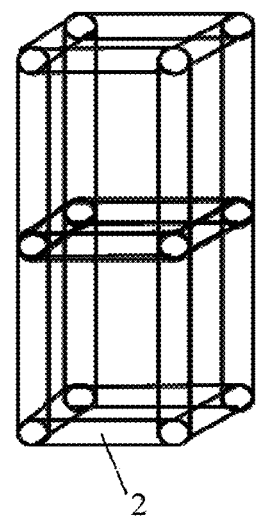

Referring to FIGS. 10A to 10C, FIGS. 10A to 10C are abridged general views of some types of the movable containing device in accordance with the present invention.

FIG. 10A is a type of the movable containing device (2) of the first embodiment. The type of the movable containing device (2) should not be limited, for example, the movable containing device (2) may be square-shaped referring to FIG. 10B, or web shaped referring to FIG. 10C.

Figure 11:
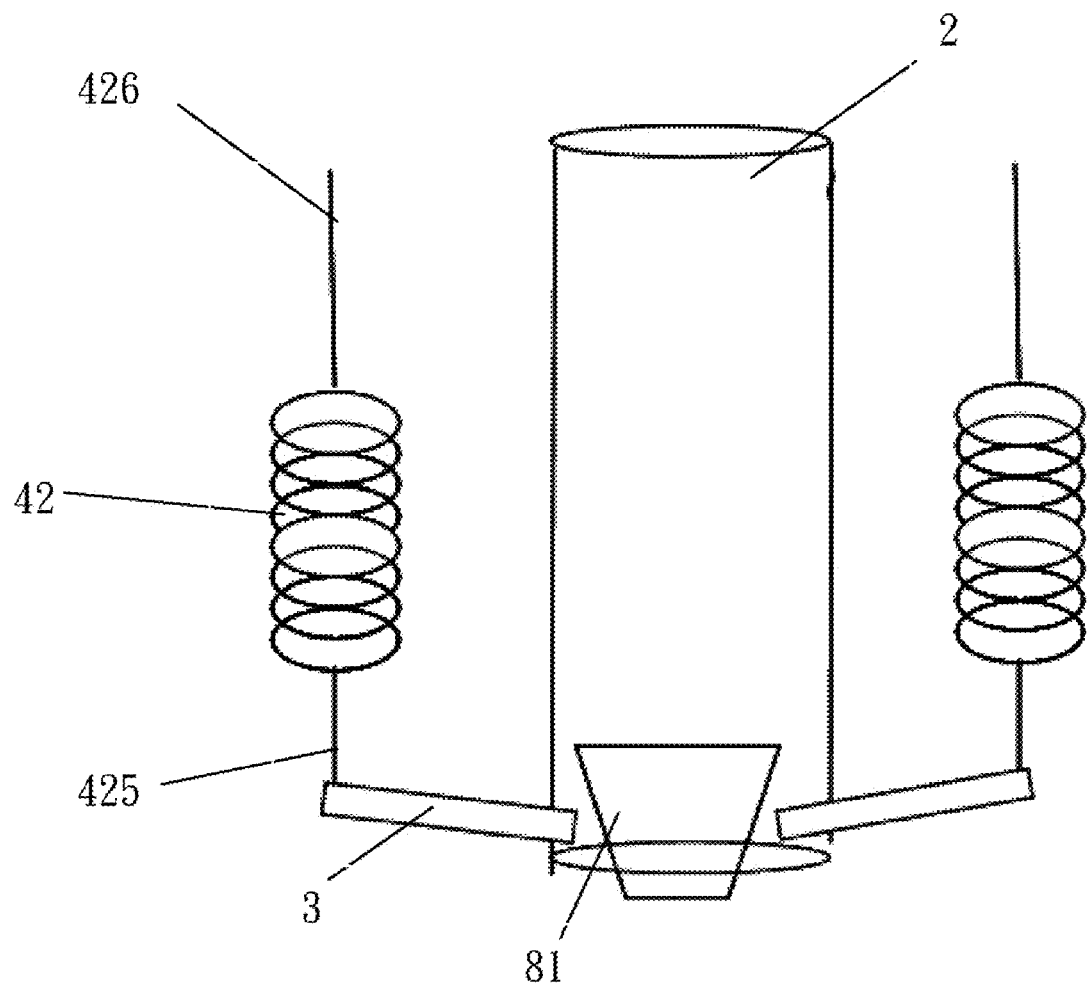
FIG. 11 is an abridged general view of another embodiment of a driving member in accordance with present invention.

Please referring to both FIG. 6C and FIG. 11, FIG. 11 is an abridged general view of another embodiment of the driving member. The driving member herein is a spring (42). One end (425) of the spring (42) connects to the shield touching portion (34) with reference to FIG. 6C, another end (426) of the spring (42) connects to the housing (1) with reference to FIG. 6C. The spring (42) in this embodiment replace the function of the shield (41) in the first embodiment. When the movable containing device (2) is moved to a predetermined position, the spring can provide a pulling force to drive the output device (3) to rotate and then to export the ear caps.

Figure 12:
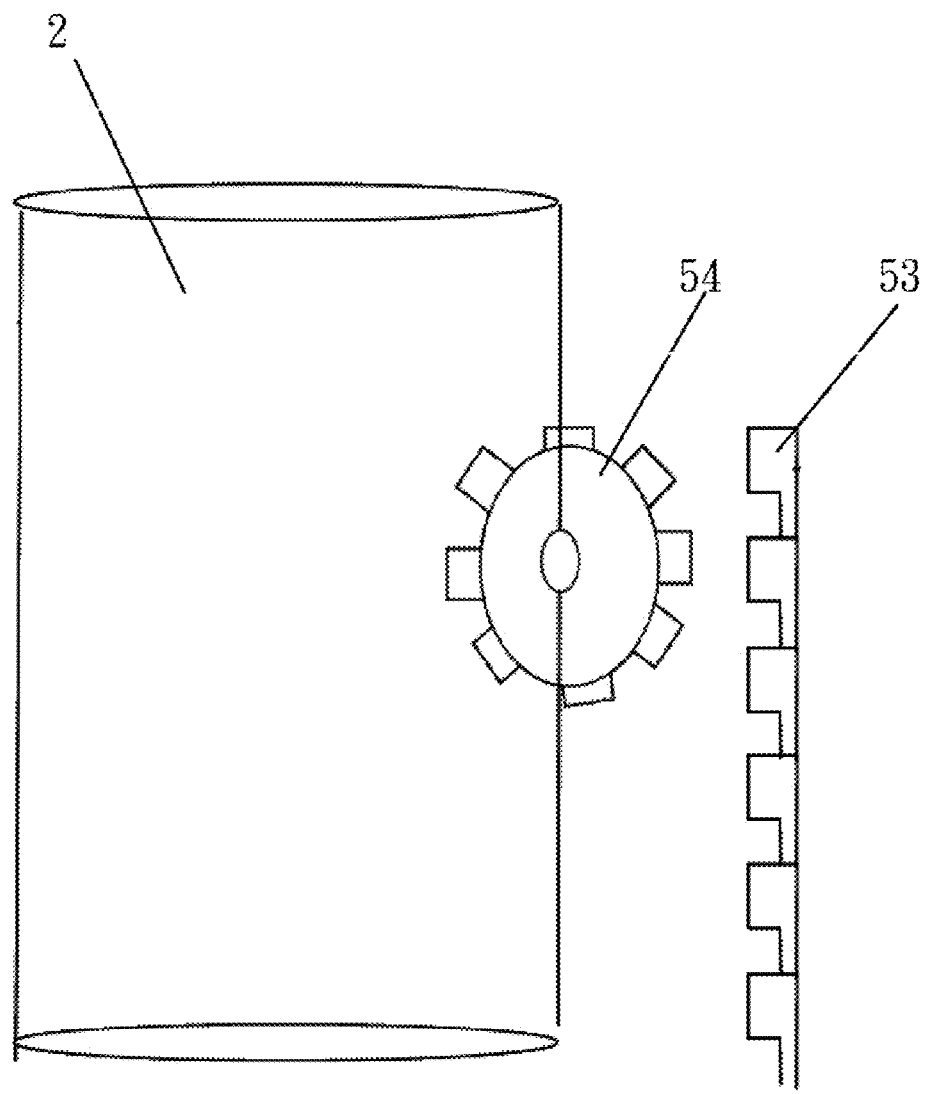
FIG. 12 is an abridged general view of another embodiment of a rail assembly in accordance with the present invention.
Figures 13A, 13B, 13C, 13D:
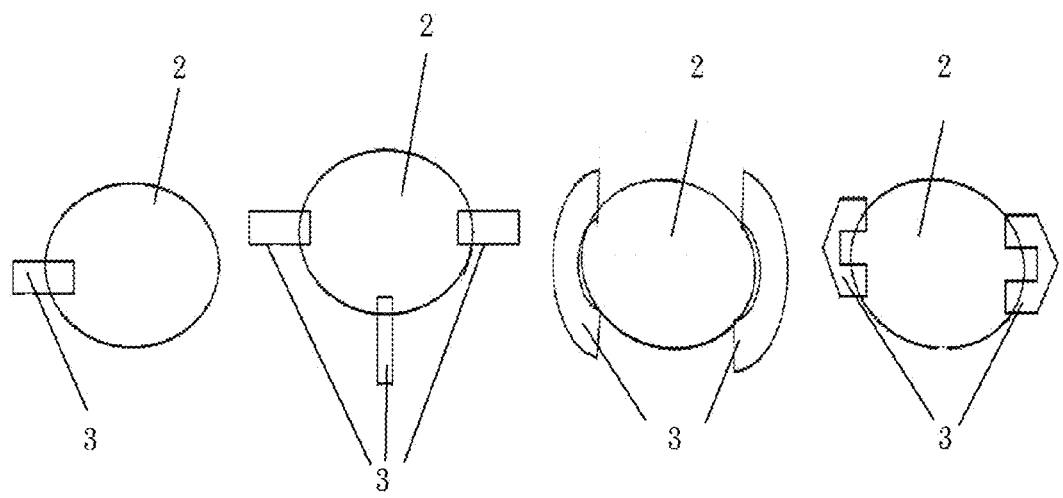
FIGS. 13A to 13D are abridged general views of other four embodiments of a disposing situation of the output device in accordance with the present invention.

Please referring to FIG. 5 and FIG. 12, FIG. 12 is an abridged general view of another embodiment of the rail assembly. In this embodiment, a rack (53) replaces the slide (51) with reference to FIG. 5 and couples with a pinion (54). The pinion (54) replaces the protrusion (52) with reference to FIG. 5.

Please refer to FIG. 6C and FIGS. 13A to 13D, FIGS. 13A to 13D are abridged general views of other four embodiments of the disposing situation of the output device.

The output devices (3) is disposed at each of the two sides of the movable containing device (2) referring to FIG. 6C of the first embodiment. The output device (3) may be disposed at one side of the movable containing device (2) with reference to FIG. 13A, multiple sides of the movable containing device (2) with reference to FIG. 13B. In other embodiment, the output device (3) may be an arc-shaped for increasing the contact area with the movable containing device (2) with reference to FIG. 13C, or a pawl-shaped for contacting the movable containing device (2) with multiple sites with reference to FIG. 13D.

Figure 14A:
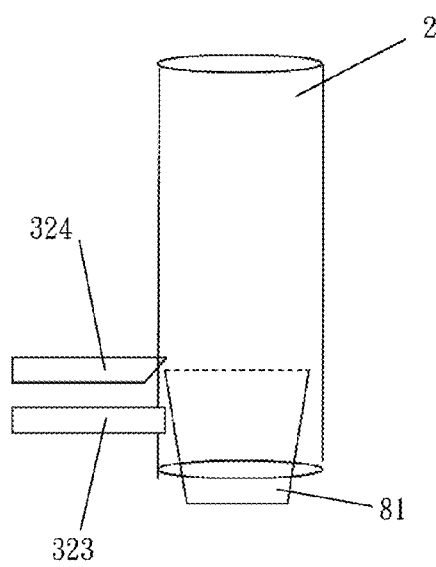
FIGS. 14A and 14B are abridged general views of other two embodiments of the output device in accordance with the present invention.
Figure 14B:
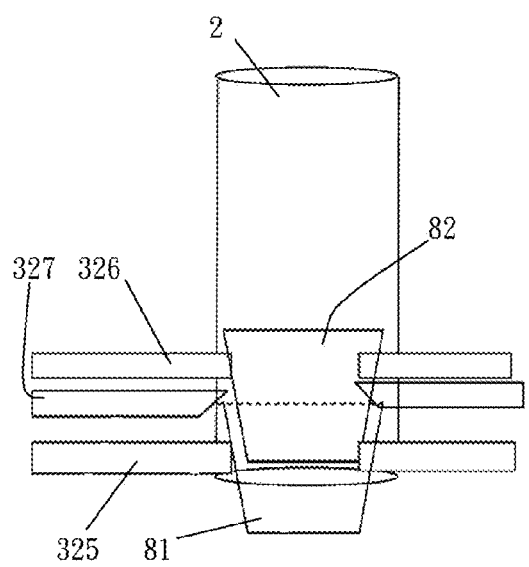

FIGS. 14A and 14B are abridged general views of other two embodiments of the output device. Please also refer to FIGS. 6C, 7C and 8C. In the first embodiment, the output device (3) is integral, and which comprises an ear cap supporting portion (32) assembled by rib (321) and rib (322). The rib (321) provides a supporting force. The rib (322) provides not only a supporting force but also a pushing force. Referring to FIG. 14A, the rib (323) and rib (324) of output device (3) are separate members that can be driven by a separate or one driving member(s) (not shown in figure). When the rib (324) is driven to move in parallel, the rib (324) can provide a pushing force as rib (322) dose. When the rib (323) is driven to move in parallel, the rib (323) provides a support force as rib (321) dose. In this embodiment, the output device can be set at one side, two sides or multiple sides of the movable containing device (2). In other embodiments, the motion of the ribs (323,324) may be designed as rotation.

In another embodiment referring to FIG. 14B, the output device may be constructed with a rib (325), a rib (326) and a pushing member (327). The rib (325) is driven by a driving member to move in parallel to provide a supporting force as rib (321) does. The rib (326) is driven by a driving member to move in parallel to provide a supporting force as rib (322) does. The pushing member (327) is driven by a driving member to move in parallel to provide a pushing force as rib (322)

does. In this embodiment, the output device can also be set at one side, two sides or multiple sides of the movable containing device (2). In other embodiments, the motion of the ribs (325,326) and the pushing member (327) may also be designed as rotating motion style.

Referring to FIGS. 15A to 15C, FIG. 15A is a perspective view of the ear cap in accordance with the present invention. FIG. 15B is a side view of the ear cap in FIG. 15A. FIG. 15C is a top view of the ear cap in FIG. 15A.

The ear cap (8) suits with the ear cap supplying device in accordance with the present invention. The ear cap (8) in accordance with the present invention comprises a cover structure, which may fit in with the probe of an ear thermometer. In this embodiment the cover structure includes a main portion (83) and a thin film (84). The main portion (83) has a cap opening (831). The thin film (84) extends from the main portion (83) and forms a closure end (86).

The main portion (83) forms as tube shaped. A tapered portion (832) between the main portion (83) and the thin film (84) may further defined. Take the first embodiment as an example, the ribs (321, 322) may contact the ear caps at the tapered portion (832) when the ear caps are contained in the movable containing device (2).

The main portion (83) and the thin film (84) of the ear cap described herein may be made of flexible plastic materials. Preferably, the flexible plastic materials are selected from the group consisting of polyethylene and polypropylene.

In some embodiments in accordance with the present invention, an ear cap set is provided (figure not shown). The ear cap set comprises multiple ear caps and an ear cap holder. The ear cap holder may be such as a plastic package or a container made from plastic, acrylic or paper. The ear cap holder is used for holding the multiple ear caps and preventing the ear caps from pollution. User can fill the ear caps from the ear cap holder to the movable containing device of the ear cap supplying device of the present invention for increasing the filling convenience of the ear caps.

Accordingly, the ear cap supplying device may not only decrease the contact with the pollutants, but also may adjust the position of the ear cap(s).

Furthermore, there are also other advantages in some embodiments of the present invention exemplarily listed as follows:

(1) It can be accurate to assist the ear cap to fall into a predetermined holding position.

(2) The position situation of the ear caps such as the number of the ear caps or the stacking situation of the ear caps can be shown, so it can be judged whether the ear cap should be added more or the position of the ear caps should be adjusted.

While the present invention has been described in terms of various specific embodiments, those skilled in the art will recognize that the present invention can be practiced with modification within the spirit and scope of the claims.

What is claimed is:

1. An ear cap supplying device comprising:
  a movable containing device for containing at least one ear cap; and
  an output device for exporting the ear cap; wherein, when said movable containing device is moved to a predetermined position, said movable containing device activizes said output device to export the ear cap(s).

2. The ear cap supplying device of claim 1, further comprising a driving member which is coupled to said output device for driving said output device.

3. The ear cap supplying device of claim 1, further comprising a rail assembly coupled to said movable containing device and used for having said movable containing device moving along said rail assembly.

4. The ear cap supplying device of claim 1, wherein said movable containing device further comprises a main body for containing the ear cap and at least one extension portion extending out from said main body for providing a holding site.

5. The ear cap supplying device of claim 1, further comprising an ear cap holding base for receiving the ear cap and disposed at a site located at a path where the ear cap exported out;
  wherein, as said movable containing device is moved from an initial position to said predetermined position, an opening of said ear cap supplying device is relatively closer to the ear cap holding base.

6. The ear cap supplying device of claim 1, further comprising an ear cap display device for displaying the disposing situation of the ear cap(s).

7. An ear cap supplying device, comprising:
  a movable containing device for containing at least one ear cap and adjusting a position of the ear cap with a motion of said movable containing device.

8. An ear cap adapted to an ear cap supplying device, and said ear cap supplying device comprising a movable containing device, said ear cap comprising:
  a cover structure which fit in with a probe of an ear thermometer; wherein said movable containing device is used for containing said ear cap, and a position of the ear cap is adjusted with a motion of said movable containing device.

9. The ear cap of claim 8, wherein said ear cap supplying device further comprises an output device, and when said movable containing device is moved to a predetermined position, said movable containing device activizes said output device to export said ear cap.

10. An ear cap set adapted to an ear cap supplying device, said ear cap supplying device comprising a movable containing device, said ear cap set comprising:
  multiple ear caps and each of them fit in with a probe of an ear thermometer; and
  an ear cap holder for holding said ear caps and for placing said ear caps into said movable containing device; wherein, with a motion of said movable containing device, a position of the ear caps in said movable containing device is adjusted.

* * * * *